United States Patent
Song et al.

(10) Patent No.: US 10,295,636 B2
(45) Date of Patent: May 21, 2019

(54) INTEGRATED CIRCUIT FOR NMR SYSTEMS

(71) Applicants: SCHLUMBERGER TECHNOLOGY CORPORATION, Sugar Land, TX (US); PRESIDENT AND FELLOWS OF HARVARD COLLEGE, Cambridge, MA (US)

(72) Inventors: Yi-qiao Song, Newton, MA (US); Jeffrey Paulsen, Brookline, MA (US); Donhee Ham, Sudbury, MA (US); Dongwan Ha, Cambridge, MA (US)

(73) Assignees: SCHLUMBERGER TECHNOLOGY CORPORATION, Sugar Land, TX (US); PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 211 days.

(21) Appl. No.: 15/032,241

(22) PCT Filed: Oct. 28, 2014

(86) PCT No.: PCT/US2014/062621
§ 371 (c)(1),
(2) Date: Apr. 26, 2016

(87) PCT Pub. No.: WO2015/066005
PCT Pub. Date: May 7, 2015

(65) Prior Publication Data
US 2016/0274204 A1    Sep. 22, 2016

Related U.S. Application Data

(60) Provisional application No. 61/896,464, filed on Oct. 28, 2013.

(51) Int. Cl.
*G01R 33/54* (2006.01)
*G01N 24/08* (2006.01)
(Continued)

(52) U.S. Cl.
CPC ........ *G01R 33/543* (2013.01); *G01N 24/081* (2013.01); *G01R 33/3607* (2013.01);
(Continued)

(58) Field of Classification Search
USPC ..................... 324/300–322; 600/407–435; 382/128–131
See application file for complete search history.

(56) References Cited

U.S. PATENT DOCUMENTS 5,285,159 A * 2/1994 Bodenhausen ...... G01R 33/446
324/307
5,629,623 A 5/1997 Sezginer et al.
(Continued)

FOREIGN PATENT DOCUMENTS

JP    1992-04-024588 A    1/1992
JP    2007-335958 A    12/2007
(Continued)

OTHER PUBLICATIONS

CMOS Mini Nuclear Magnetic Resonance System and its Application for Biomolecular Sensing, 2008 IEEE International Solid-State Circuits Conference, Session 7, TD: Electronics for Life Sciences, 7.3, 2008.
(Continued)

*Primary Examiner* — Tung X Nguyen
*Assistant Examiner* — Robert P Alejnikov, Jr.
(74) *Attorney, Agent, or Firm* — Gordon & Jacobson, P.C.

(57) ABSTRACT

An integrated circuit is provided for use in conjunction with an external antenna. The integrated circuit includes a
(Continued)

memory circuit, a pulse sequencer, an NMR transmitter circuit and an NMR receiver circuit. The memory circuit is configured to store user-defined parameter data pertaining to an excitation period and an acquisition period that are part of an NMR pulse sequence. The pulse sequencer and the NMR transmitter circuit are configured to cooperate to generate RF signals in accordance the user-defined parameter data stored in the memory circuit, wherein such RF signals are supplied to the external antenna for emitting excitation signals from the external antenna during the excitation period of the NMR pulse sequence. The NMR receiver circuit is configured to receive electrical signals generated by the external antenna during the acquisition period of the NMR pulse sequence.

29 Claims, 12 Drawing Sheets

(51) Int. Cl.
  *G01R 33/36* (2006.01)
  *G01V 3/32* (2006.01)
  *G01R 33/3415* (2006.01)

(52) U.S. Cl.
  CPC ..... *G01R 33/3614* (2013.01); *G01R 33/3621* (2013.01); *G01V 3/32* (2013.01); *G01R 33/3415* (2013.01); *G01R 33/3635* (2013.01)

(56) References Cited

U.S. PATENT DOCUMENTS

| | | | |
|---|---|---|---|
| 6,392,410 | B2 | 5/2002 | Luong et al. |
| 6,400,147 | B1 * | 6/2002 | Toufaily ............... G01N 24/081 324/300 |
| 6,570,382 | B1 | 5/2003 | Hurlimann et al. |
| 6,960,913 | B2 | 11/2005 | Heaton |
| 7,053,611 | B2 | 5/2006 | Freedman |
| 7,129,871 | B1 * | 10/2006 | Venes ................. H03F 3/45089 341/136 |
| 8,115,485 | B1 * | 2/2012 | Maier ................. G01R 33/543 324/307 |
| 2010/0164495 | A1 * | 7/2010 | Takizawa ............ G01R 33/482 324/309 |
| 2011/0057654 | A1 | 3/2011 | Sun et al. |
| 2011/0066041 | A1 * | 3/2011 | Pandia ................... A61B 5/029 600/484 |
| 2011/0187372 | A1 * | 8/2011 | Kruspe ................ G01N 24/081 324/333 |
| 2011/0213235 | A1 * | 9/2011 | Arai ...................... G01R 33/583 600/410 |
| 2012/0235677 | A1 * | 9/2012 | Blanz .................. G01N 24/081 324/303 |
| 2013/0154635 | A1 | 6/2013 | Mandal et al. |
| 2013/0176026 | A1 | 7/2013 | Song et al. |
| 2013/0234706 | A1 * | 9/2013 | Mandal ............... G01N 24/081 324/303 |
| 2014/0184220 | A1 | 7/2014 | Paulsen et al. |

FOREIGN PATENT DOCUMENTS

| | | |
|---|---|---|
| WO | WO92/09901 A1 | 6/1992 |
| WO | WO2012/110901 A1 | 8/2012 |

OTHER PUBLICATIONS

CMOS RF Biosensor Utilizing Nuclear Magnetic Resonance, Nan Sun et al., IEEE Journal of Solid-State Circuits, vol. 44, No. 5, May 2009, pp. 1629-1643.

Palm NMR and 1-Chip NMR, Nan Sun et al., Nan Sun et al., IEEE Journal of Solid-State Circuits, vol. 46, No. 1, Jan. 2011, pp. 342-352.

* cited by examiner

| Pulse width | Pulse amplitude | Pulse phase | Spacing | Quench | Acquisition | Loop start | Loop end |
|---|---|---|---|---|---|---|---|
| 24 bit | 5 bit | 5 bit | 24 bit | 3 bit | 1 bit | 1 bit | 1 bit |
| <63:40> | <39:35> | <34:30> | <29:6> | <5:3> | <2> | <1> | <0> |

INTEGRATED CIRCUIT FOR NMR SYSTEMS

CROSS-REFERENCE TO RELATED APPLICATIONS

The present application claims priority from U.S. Provisional Application No. 61/896,464, entitled "IC-based NMR systems", filed on Oct. 28, 2013, herein incorporated by reference in its entirety.

GOVERNMENT LICENSE RIGHTS

This invention was made with government support under 1231319 awarded by National Science Foundation. The government has certain rights in the invention.

FIELD

The present application relates generally to NMR (nuclear magnetic resonance) systems and methods.

BACKGROUND

Nuclear Magnetic Resonance (NMR) spectrometers have been in use for many years and can be used to provide imaging and/or analysis of a sample being tested. In general, a typical single channel NMR spectrometer is comprised of three main components: a pulse sequencer, an NMR transmitter, and an NMR receiver. The NMR transmitter and the NMR receiver both interface to an external antenna (i.e., coil) that is typically part of an NMR probe that receives the sample. An external magnet can also be provided to provide a static magnetic field (typically referred to as the $B_0$ field) to the sample during NMR experiments. The pulse sequencer and the NMR transmitter cooperate to supply a train of pulses of an oscillating RF (radiofrequency) signal to the external antenna in order to excite macroscopic nuclear spins in the sample. The NMR receiver receives NMR signals detected by the external antenna and amplifies the received NMR signals with low noise and high gain. The NMR signals produced by the NMR receiver are processed by signal processing circuitry (typically involving digitization by an analog-to-digital converter and data processing by a data processor) in order to derive useful physical and chemical information.

NMR logging is an established type of NMR measurement wherein an NMR spectrometer is lowered into a borehole in the earth, and NMR measurements are performed to determine properties within and/or surrounding the borehole. However, existing NMR logging spectrometers have a number of drawbacks, including high expense and support for a limited pulse sequence format for the NMR experiments. Furthermore, the downhole sensor package designed to fit within the borehole can be large in size and very heavy.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In an embodiment of the subject disclosure, an integrated circuit (IC) is provided that includes a memory circuit, pulse sequencer, an NMR transmitter circuit, and an NMR receiver circuit. The IC can be realized by a monolithic IC, such as an ASIC (application specific integrated circuit) and/or a CMOS (complementary metal-oxide-semiconductor) integrated circuit. The memory circuit is configured to store user-defined parameter data pertaining to an excitation period and an acquisition period that are part of an NMR pulse sequence. The pulse sequencer and the NMR transmitter circuit cooperate to generate RF signals in accordance the user-defined parameter data stored in the memory circuit, wherein such RF signals are supplied to the external antenna for emitting excitation signals from the external antenna during the excitation period of the NMR pulse sequence. The NMR receiver circuit receives electrical signals generated by the external antenna during the acquisition period of the NMR pulse sequence.

In another aspect, a multi-channel NMR system is provided that includes a plurality of integrated circuits as described herein, wherein the pulse sequencer of each respective integrated circuit initiates NMR experiments involving at least one NMR pulse sequence in response to an Enable signal communicated to the respective integrated circuit.

In yet another aspect, An NMR apparatus includes a host system and at least one integrated circuit as described herein, including a data communication interface to the host system. The data communication interface receives the user-defined parameter data from the host system and transfers the received user-defined parameter data to the memory circuit of the integrated circuit for storage therein. The at least one integrated circuit can further include at least one output port for outputting electrical signals in analog form as generated by the NMR receiver circuit of the integrated circuit. The NMR apparatus can further include signal processing circuitry, operably coupled to the at least one output port, for processing the electrical signals output from the output port.

Further features and advantages of the subject application will become more readily apparent from the following detailed description when taken in conjunction with the accompanying drawings.

BRIEF DESCRIPTION OF THE DRAWINGS

The present application is further described in the detailed description which follows, and in reference to the noted plurality of drawings by way of non-limiting examples of embodiments of the present application, in which like reference numerals represent similar parts throughout the several views of the drawings.

DETAILED DESCRIPTION

Illustrative embodiments of the present disclosure are directed to an integrated circuit for a nuclear magnetic resonance (NMR) system. The integrated circuit is provided for use in conjunction with an external antenna. The integrated circuit can include a memory circuit, a pulse sequencer, an NMR transmitter circuit and an NMR receiver circuit. The memory circuit is configured to store user-defined parameter data pertaining to an excitation period and an acquisition period that are part of an NMR pulse sequence. The pulse sequencer and the NMR transmitter circuit are configured to cooperate to generate RF signals in accordance the user-defined parameter data stored in the memory circuit, wherein such RF signals are supplied to the external antenna for emitting excitation signals from the external antenna during the excitation period of the NMR pulse sequence. The NMR receiver circuit is configured to receive electrical signals generated by the external antenna during the acquisition period of the NMR pulse sequence. Details of various embodiments are discussed below.

Figure 1:
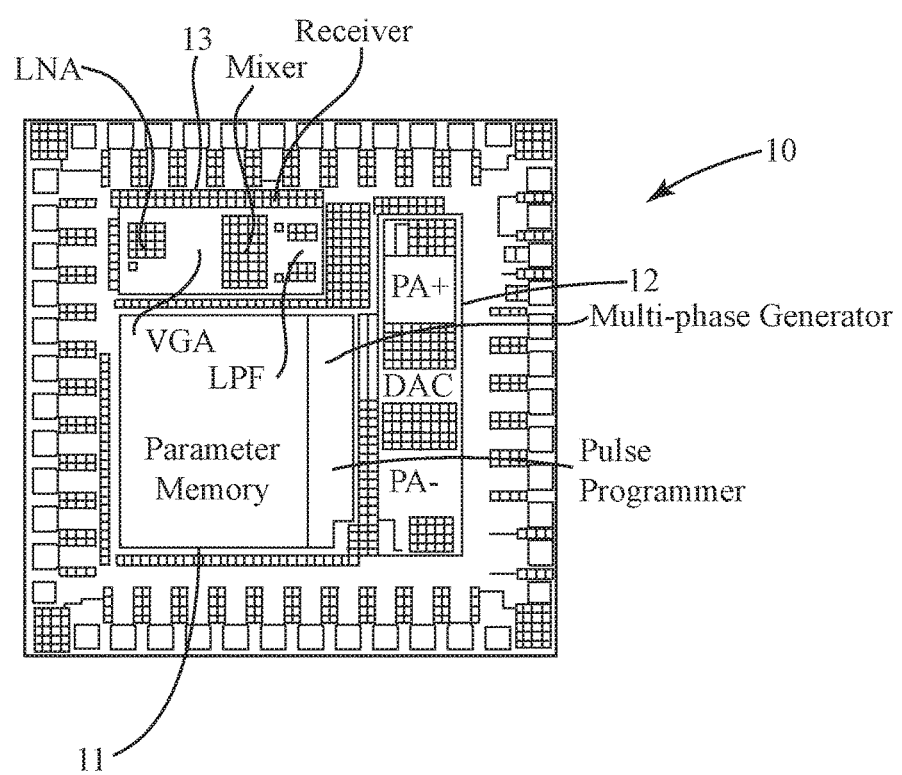
FIG. 1 is a photograph of an NMR ASIC in accordance with some embodiments of the present application.

FIG. 1 illustrates an embodiment of an NMR ASIC 10 in accordance with the present application, which integrates a digitally-programmable pulse sequencer 11, a digitally-controlled NMR transmitter 12, and a digitally-controlled NMR receiver 13 integrated as parts of a single integrated circuit chip within an area of about 4 mm$^2$. Other embodiments may use integrated circuit chips having different dimensions. The NMR ASIC 10 can be fabricated using commercially available process technology (such as the TSMC 0.18 µm process of Taiwan Semiconductor Manufacturing Company, Limited or TSMC). The NMR receiver 13 can be temperature compensated so that the gain of the NMR receiver 13 is insensitive to expected variations in temperature during operation of the NMR ASIC 10. This feature can improve performance of the NMR ASIC 10 at high temperatures.

The digitally-programmable pulse sequencer 11 and the digitally-controlled NMR transmitter 12 of the NMR ASIC 10 can be configured such that the NMR transmitter 12 generates a wide variety of NMR pulse sequences (i.e., sequences of pulses of oscillating RF signals that are supplied to an external antenna in order to excite macroscopic nuclear spins in a sample). This feature allows multiple NMR pulse sequences to be tested and used with the NMR ASIC 10 for different NMR experiments without hardware modification to the NMR ASIC 10. This feature is useful for research and development of novel NMR technologies as well as deployment of the technology to the field.

Figure 2:
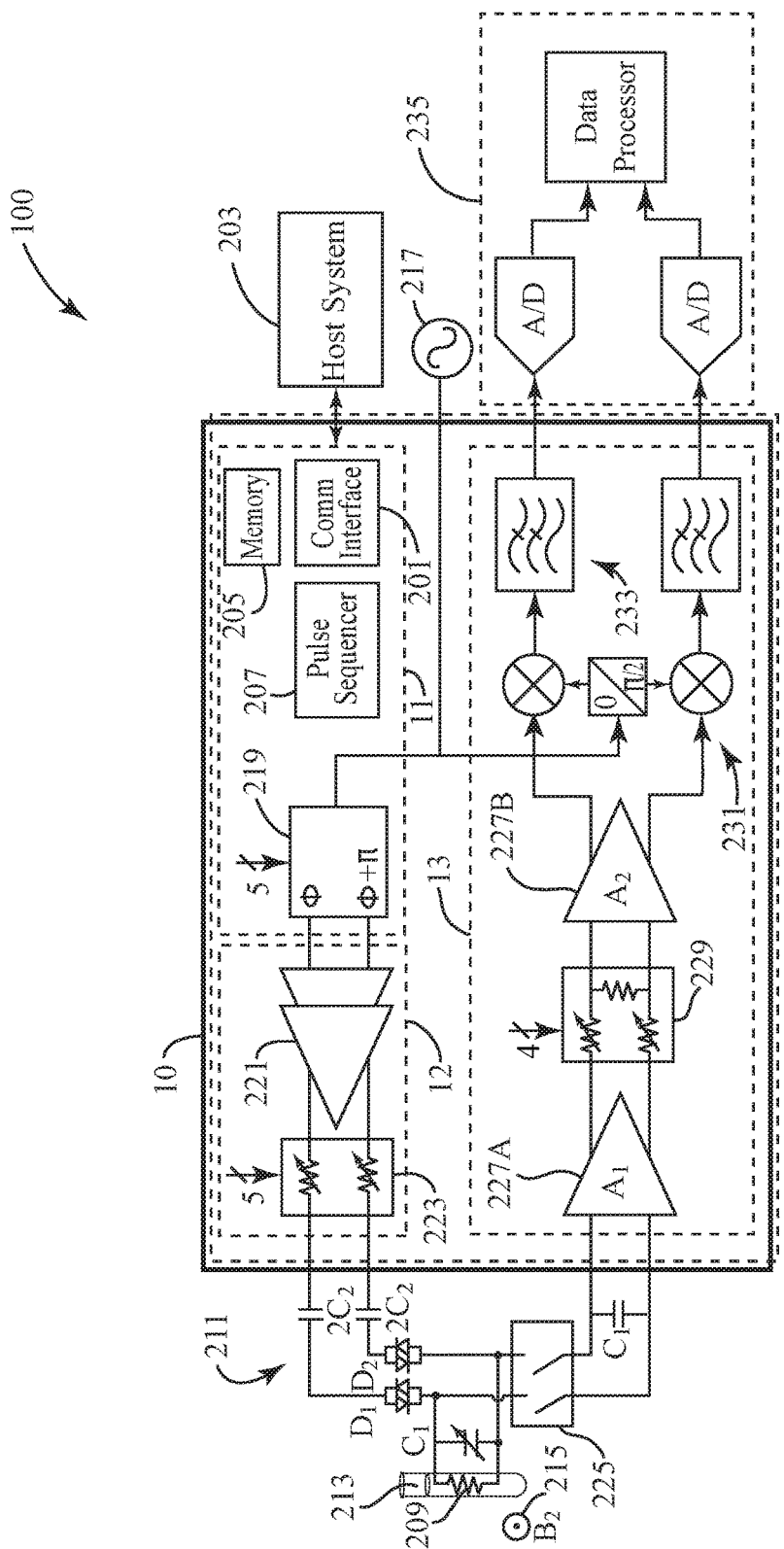
FIG. 2 is a functional block diagram of an NMR ASIC in accordance with some embodiments of the present application as well as an NMR spectrometer that that employs such NMR ASIC.

FIG. 2 illustrates the architecture of an embodiment of the NMR ASIC 10 as well as an NMR spectrometer 100 that employs such NMR ASIC 10. The digitally-programmable pulse sequencer 11 of the NMR ASIC 10 includes a communication interface 201 that interfaces with a host system 203 to receive data (user-defined parameter data) representative of one or more user-defined parameters that pertain to an excitation period and an acquisition period that are part of an NMR pulse sequence as shown schematically in FIG. 3. Such user-defined parameter data can represent (i) time duration for the excitation period, (ii) a pulse amplitude for excitation signals that are part of the NMR pulse sequence, (iii) a pulse phase for such excitation signals, (iv) a time duration for the acquisition period, (v) a time period between the excitation period and the acquisition period (labeled as "Quench" in FIG. 3), (vi) a loop start and a loop end for a loop of NMR pulse sequences, (vii) information that dictates the gain of the NMR receiver 13 during the acquisition period, and (viii) information that enables or disables the NMR receiver 13 during the acquisition period. The host system 203 can be a commercially-available microcontroller or digital signal processor or other data processing system. The host system 203 can employ a graphical user interface or user input mechanism that allows a user to define (or select) the user-defined parameter data and transfer such data to the digitally-programmable pulse sequencer 11 of the NMR ASIC 10. The digitally-programmable pulse sequencer 11 also includes a memory circuit 205 (such as a register file) that stores the user-defined parameter data as received by the communication interface 201. The communication interface 201 can utilize standard communication protocols to communicate with the host system 203, including but not limited to the Serial Peripheral Interface (SPI) protocol, the RS-422 interface protocol, wired and wireless USB protocols, wireless Bluetooth® protocol or other suitable data communication interface. The communication interface 201 of the pulse sequencer 11 allows the NMR ASIC 10 IC to operate either as a standalone NMR apparatus, or as a satellite sensor, which makes it suitable for multiple channel NMR applications.

During NMR experiments, the user-defined parameter data is stored in the memory circuit 205 and is accessed and used by the pulse sequencer circuit 207 to generate digital control signals that are supplied to the digitally-controlled NMR transmitter 12 and the digitally-controlled NMR receiver 13 of the NMR ASIC 10 in order to control operations of the NMR transmitter 12 and the NMR receiver 13 during such NMR experiments in accordance with the user-defined pulse parameter data stored in the memory circuit 205. For example, the NMR transmitter 12 and/or the NMR receiver 13 can include a digitally-controlled attenuator stage as described below, whose level of attenuation can be controlled during such NMR experiments in accordance with the user-defined parameter data stored in the memory circuit 205. Other parts of the NMR transmitter 12 and/or other parts of the NMR receiver 13 can also be controlled in accordance with the user-defined parameter data stored in the memory circuit 205.

The NMR transmitter 12 interfaces to an external antenna 209 (i.e., RF coil) via a capacitor and diode network 211. The capacitors of the network 211 can be configured such that the impedance of the circuit matches the inductance of the antenna 209. The diodes of the network 211 can be configured as a duplexer to provide for conduction across the diodes during the excitation period of an NMR pulse sequence and isolation of the NMR receiver 13 from the NMR transmitter 12 in the acquisition period of the NMR pulse sequence. The antenna 209 can be part of an NMR probe 213 that receives the sample. An external magnet 215 can also be provided to provide a static magnetic field (commonly referred to as the $B_0$ field) to the sample during the NMR experiments.

An external clock generator 217 generates a reference oscillating RF signal at the Larmor frequency. This reference oscillating RF signal is supplied to a phase generator circuit 219 of the pulse sequencer 11. The pulse sequencer circuit 207 operates to generate digital control signals that are supplied to the multi-phase generator circuit 219 such that multi-phase generator circuit 219 generates a sequence of pulses of an oscillating RF signal ($\Phi$) at the Larmor frequency at a digitally-controlled phase offset relative to the reference oscillating RF signal along with an oscillating RF signal at the Larmor frequency at quadrature phase ($\Phi+\pi$). This digital-controlled phase offset can be dictated by the user-defined parameter data stored in the memory circuitry 205 and supplied to the multi-phase generator circuit 219 by the pulse sequencer circuit 207.

The NMR transmitter 12 can provide for variable gain amplification of the pulse signals ($\Phi$, $\Phi+\pi$) generated by the multi-phase generator circuit 219 for output to the external antenna 209. The variable gain can be dictated by the user-defined parameter data stored in the memory circuity 205 and supplied to the NMR transmitter 12 by the pulse sequencer circuit 207. In one embodiment, the NMR transmitter 12 can include a power amplifier stage 221 and a digitally-controlled voltage attenuator stage 223 that process the pulse signals ($\Phi$, $\Phi+\pi$) generated by the multi-phase generator circuit 219 for output to the external antenna 209. The power amplifier stage 221 provides linear amplification of the power of the pulse signals ($\Phi$, $\Phi+\pi$). The digitally-controlled voltage attenuator stage 223 can provide controlled attenuation of the voltage level of the pulse signals ($\Phi$, $\Phi+\pi$). The amount of attenuation can be controlled according to user-defined parameter data stored in the memory circuit 205, or controlled by additional digital inputs to the ASIC. The duration of the pulse is controlled according to the pulse width parameter data stored in the memory circuit 205. The pulse width parameter data is loaded into a countdown clock that decrements the parameter by 1 at each clock cycle. In this manner, the components of the NMR transmitter 12 are capable of generating NMR pulse sequences with pulses of different amplitudes, phases and durations according to the user-defined pulse parameter data stored in the memory circuit 205, so that the nuclear spins in the sample can be manipulated deliberately.

The NMR receiver 13 of the NMR ASIC 10 interfaces to the external antenna 209 by external receive switching circuitry 225. The NMR receiver 13 can provide for variable gain amplification of the NMR signals detected by the external antenna 209, which is, for example, the free induction decay (FID) generated by non-equilibrium nuclear spin magnetization precessing about the magnetic field. The variable gain can be dictated by the user-defined parameter data stored in the memory circuitry 205 and supplied to the NMR receiver 13 by the pulse sequencer circuit 207, or by additional digital inputs. In one example, the NMR receiver 13 can include two low-noise amplifier stages 227A, 227B of fixed signal gain for low noise amplification of the NMR signals detected by the external antenna 209. A digitally-controlled voltage attenuator stage 229 can be coupled between the two low-noise amplifier stages 227A, 227B and used to control the signal gain of the NMR receiver 13 based on user-defined parameter data that dictates the gain of the NMR receiver as stored in the memory circuit 205. Such operations can be used to adjust or tune the signal gain of the NMR receiver 13 for different antennas 209. The receive switching circuitry 225 can be controlled to physically or electronically disconnect the antenna 209 and the NMR transmitter 12 from the NMR receiver 13 of the NMR ASIC 10 at the desired time intervals outside the acquisition period of the NMR pulse sequence as dictated by the time duration data for the periods of the NMR pulse sequence as stored in the memory circuit 205 (i.e., the data representing the time duration for the excitation period, the data representing time period between the excitation period and the acquisition period, and the data representing time duration for the acquisition period). The receive switching circuitry 225 can also be controlled to physically or electronically connect the antenna 209 to the NMR receiver 13 of the NMR ASIC 10 at the desired time intervals of the acquisition period of the NMR pulse sequence as dictated by the time duration data for the periods of the NMR pulse sequence as stored in the memory circuit 205.

The NMR receiver 13 can also include a quadrature heterodyne demodulator stage 231 and a low pass filter stage 233 as shown in FIG. 2. The quadrature heterodyne demodulator stage 231 is supplied with the reference oscillating RF signal generated by the clock generator 217. The quadrature heterodyne demodulator stage 231 processes the amplified NMR signals output by the amplifier stage 227B to generate an in-phase signal component (where the reference oscillating RF signal is mixed with the amplified NMR signal output by the amplifier stage 227B) and a quadrature-phase single component (where the quadrature phase of the reference oscillating RF signal is mixed with the amplified NMR signal output by the amplifier stage 227B). Both the in-phase and quadrature phase signal components generated by the quadrature heterodyne demodulator stage 231 are subjected to low pass filtering by the low pass filter stage 233. The filtered in-phase and quadrature phase signal components output by the low pass filter stage 233 can be supplied to signal processing circuitry 235, which can include a dual-channel digitizer (i.e., a dual-channel analog-to-digital converter) and associated data processor as shown. As most NMR signals exhibit a narrow frequency bandwidth as compared to the Larmor frequency, a low frequency filter removes the noise outside the NMR signal bandwidth and thus improves signal-to-noise ratio of the NMR signal. The analog-to-digital converters translate analog NMR signals into digital form and thus obtained digital signals can be further processed, such as digital filtering, optimal filter, Fourier transform, etc. The characteristics of the signals, such as amplitude, phase, frequency components, etc., can be used to determine the properties of the sample (e.g. chemical composition, physical properties, viscosity, hydrogen density, etc.). The signal processing circuitry 235 (and/or portions therefor) can be achieved in the NMR receiver 13, or the filtered data can be further transmitted to a data processor for analysis. The data processor can be part of the host system 203 or a separate system. In this manner, the NMR receiver 13 can be configured to process NMR signals during the acquisition period of one or more NMR pulse sequences, and arbitrary acquisition patterns can be performed.

As described above, the digitally-programmable pulse sequencer 11 and the NMR transmitter 12 of the NMR ASIC 10 can be configured to generate an NMR pulse sequence that perturbs the spin system of the sample so that useful physical and chemical information can be extracted from the NMR signals received by the NMR receiver 13. For example, the received NMR signals can be digitized and processed by the signal processor 235 to measure the spin echo amplitude for one or more NMR pulse sequences. From these NMR measurements, the diffusion coefficient D, as well as other properties of the sample can be derived. The NMR measurements thus obtained are "diffusion encoded" and can be inverted to produce a multi-dimensional distribution function relating to fluid properties of the sample. The multi-dimensional distribution can be a two dimensional (2-D) distribution function $f(D,T_2)$ relating the diffusion coefficient D to the spin-spin ($T_2$) relaxation times of the sample, a 2-D distribution function $f(D,T_1)$ relating the diffusion coefficient D to the spin-lattice relaxation time $T_1$ of the sample, or a three-dimensional (3-D) distribution function $f(D,T_1, T_2)$ relating the diffusion coefficient D to the spin-lattice relaxation time $T_1$ and the spin-spin relaxation time $T_2$ of the sample. Examples of such inversion techniques are described in detail in U.S. Pat. Nos. 6,570,382; 6,960,913; and 7,053,611, herein incorporated by reference in their entireties. Other analysis methods, such as Fourier transform can also be used to process the NMR data to obtain frequency spectrum where the individual peaks at different frequencies could be used to represent molecular species and their distribution in the sample. Multiple dimensional spectroscopy experiments can be performed to elucidate molecular structures, dynamics, and molecular interaction. Examples of such experiments are COSY (correlation spectroscopy), NOESY (Nuclear Overhauser Effect spectroscopy), TOCSY (total correlation spectroscopy), HMQC (heteronuclear multi-quantum coherence spectroscopy), etc.

Figure 4:
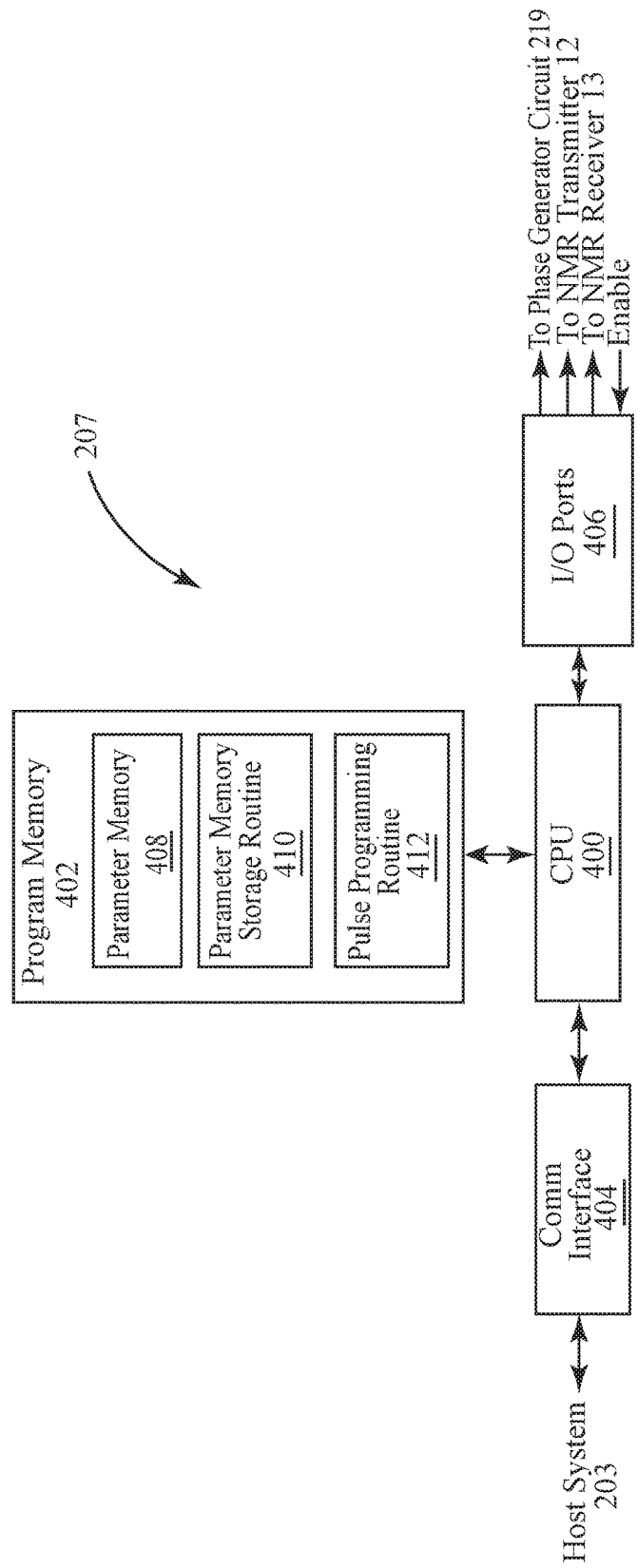
FIG. 4 is a schematic diagram of an embodiment of the pulse sequencer of the NMR ASIC of FIG. 2.

FIG. 4 is a block diagram that illustrates an embodiment of the pulse sequencer circuit 207 of FIG. 2, which is realized by a programmed controller that includes a CPU 400, program memory 402, a communication interface 404 (such as an SPI interface) to the host system 203, and Input/Output (I/O) ports 406 with corresponding data paths to the multi-phase generator circuit 219, the NMR transmitter 12 and the NMR receiver 13.

Figures 3, 5:
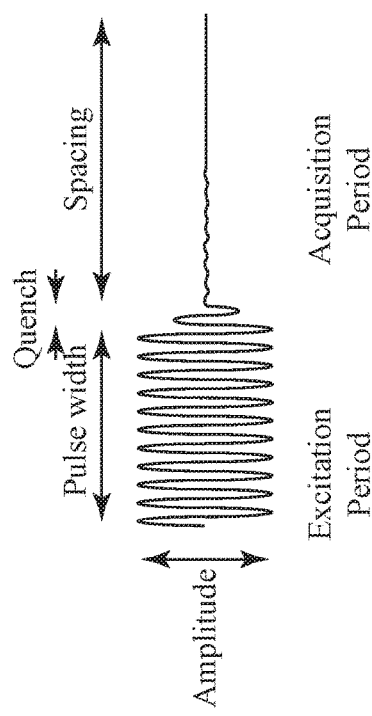
FIG. 3 is a schematic diagram of an NMR pulse sequence.
FIG. 5 is diagram of the organization of a 64-bit vector of parameter data that can be stored in the parameter memory of FIG. 4.

The program memory 402 includes memory space 408 (labeled "parameter memory") that is configured to store up to a predefined number of fixed-size bit vectors representative of a number of user-defined parameters that pertain to an excitation period and an acquisition period that are part of an NMR pulse sequence as shown schematically in FIG. 3. Such user-defined parameter data can represent time duration for the excitation period, a pulse amplitude for excitation signals that are part of the NMR pulse sequence, a pulse phase for such excitation signals, a time duration for the acquisition period, a time period between the excitation period and the acquisition period (labeled as "Quench" in FIG. 3), a loop start and a loop end for a loop of NMR pulse sequences, information that dictates the gain of the NMR receiver 13 during the acquisition period, and information that enables or disables the NMR receiver 12 during the acquisition period. In one embodiment, the parameter memory 408 can store up to 64 fixed-size bit vectors that are 64-bits in length and arranged as shown in FIG. 5. Bits <0> and <1> represent the loop end and loop start for a given loop of NMR sequences. Bit <2> represents information that enables or disables the NMR receiver 12 during the acquisition period. Bits <3>-<5> represent the duration of the time period between the excitation period and the acquisition period (labeled as "Quench" in FIG. 3). Bits <6>-<29> represent the duration of the acquisition period. Bits <30>-<34> represent the pulse phase for the excitation signals of the NMR pulse sequence. Bits <35>-<39> represent the pulse amplitude for the excitation signals of the NMR pulse sequence. Bits <40>-<63> represent the pulse width for the excitation signals (or the time duration of the excitation period) of the NMR pulse sequence. In this manner, the 64-bit vector can describe a pulse, or a delay, or a combined pulse and delay. A complete pulse sequence is described as a list of vectors. For example, a FID (free induction decay) pulse sequence can be described by the list of 4 vectors: delay of 1 s, RF pulse of 10 us, a short delay (10 us), and a delay of 0.1 s with acquisition.

The program memory 402 also stores programmed instructions for two routines that are executed by CPU 400, including a parameter memory storage routine 410 and a pulse programming routine 412. The communication interface 404 interfaces with the host system 203 to receive the fixed-size bit vectors representative of the user-defined pulse parameters as described above. The execution of the instructions of the parameter memory storage routine 410 by the CPU 400 cooperates with the communication interface 404 to write the fixed-size bit vectors received by communication interface 404 into the parameter memory 408. The execution of the instructions of the pulse programming routine 412 by the CPU 400 cooperates with the I/O ports 406 to receive an Enable signal and to supply digital control signals to the phase generator 219, the NMR transmitter 12 and the NMR receiver 13 as needed to carry out an NMR experiment involving one or more NMR pulse sequences as dictated by the fixed-size bit vector(s) stored in the parameter memory 408. Such NMR experiments can involve NMR pulse sequences of varying amplitudes, phases, and durations (which are constrained by the size of the parameter memory 408 and the maximum power level of the NMR transmitter 12).

In an illustrated embodiment where the parameter memory 408 can store up to 64 fixed-size bit vectors that are 64-bits in length and arranged as shown in FIG. 5, the execution of the instructions of the pulse programming routine 412 by the CPU 400 can be configured such that the NMR transmitter generates a train of up to 64 NMR pulses with individual amplitude, phase and duration for each NMR pulse sequence. Each NMR pulse sequence contains an excitation signal (one RF pulse) generated during an excitation period. An acquisition period follows the excitation period after a quench period as shown in FIG. 3. The NMR transmitter 12 is decoupled from the antenna 209 during the acquisition period. Bits <40>-<63> are used to control the pulse width of the excitation signals (i.e., the time duration of the excitation period) of the NMR pulse sequence. Bits <3>-<5> are used to control the quench period. Bits <6>-<29> are used to control the duration of the acquisition period. The NMR receiver 13 can be selectively enabled (i.e., selectively coupled to the antenna 209 by the receiver switching circuitry 225) during the acquisition period as dictated by the bit value of Bit <2> of the corresponding 64-bit vector for the given NMR pulse. The execution of the instructions of the pulse programming routine 412 by the CPU 400 accesses one 64-bit vector at a time and controls the NMR transmitter 12 to generate the specified excitation signals for the specified duration of the excitation period to the antenna 209 and/or controls the NMR receiver 13 to acquire the NMR signal as received from the antenna 209 for the specified duration of the acquisition period.

The instructions of the pulse programming routine 412 by the CPU 400 can employ a pulse address register that indicates the current pulse parameter address and stores the address to return in a loop if configured. A loop can be specified by bits <0> and <1> of the 64-bit vector. One bit (bit <1>, the loop-start bit) indicates the beginning of the loop and the other bit (bit <0>, the loop-end bit) indicates the end of the loop-end. In the event that the loop-end bit is set in the current 64-bit vector, the address of the 64-bit vector with the loop start-bit already set is used for the next NMR pulse sequence. This looping structure allows the execution of repeated pulse segments (several RF pulses and delays, and the associated acquisition period as a group), such as CPMG pulse sequence or related ones.

The instructions of the pulse programming routine 412 by the CPU 400 can also be configured to control the amplitude of the excitation signals of each NMR pulse sequence as dictated by bits <35>-<39> of the corresponding 64-bit vector The instructions of the pulse programming routine 412 by the CPU 400 can also be configured to control the phase of the excitation signals of each NMR pulse sequence as dictated by bits <30>-<34> of the corresponding 64-bit vector. This allows the phase of the excitation signal to be set to any one of a number of allowed values for every excitation signal (pulse) during each given NMR pulse sequence. This feature is useful for phase cycling technique and for advanced pulse design. It also allows multiple phases to be used and shifted during a set of pulse sequences. This feature can be useful e.g. for phase cycling technique or for advanced pulse design such as composite pulses.

The instructions of the pulse programming routine 412 by the CPU 400 can also be configured to initiate the set of individual pulse sequences as dictated by the 64-bit parameter vectors stored in the parameter memory 408 in response to receiving an Enable signal supplied to the I/O ports 406 as shown in FIG. 4. This feature is useful for synchronization of NMR experiments across multiple NMR ASICs 10.

Note that the illustrative embodiment allows the instructions of the pulse programming routine 412 by the CPU 400 to carry out a set of 64 individual NMR pulses. The number of NMR pulse sequences in the set can be increased by expanding the parameter memory 408 without changing the protocol. Also, more complex RF pulse parameter formats (more than 64 bits, for example, such as 128 bits) can be used to describe the properties of the pulses, which will increase the on-chip memory requirement.

Figure 6:
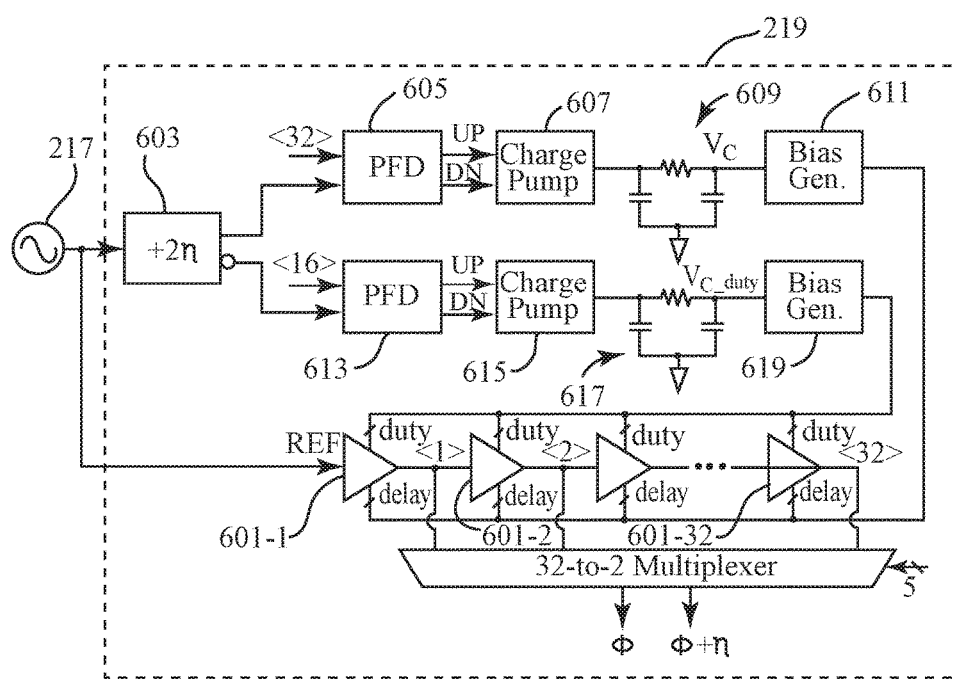
FIG. 6 is a schematic diagram of an embodiment of the multiphase generator circuit of the NMR ASIC of FIG. 2.

FIG. 6 illustrates an embodiment multi-phase generator circuit 219 of FIG. 2, which is based on a delay-locked loop (DLL). The DLL is supplied with the reference oscillating RF signal as generated by the clock generator 217. The reference oscillating RF signal can have a frequency from a few kHz to 60 MHz. This reference oscillating RF signal is supplied in parallel to a delay line that includes thirty-two series-coupled delay cells 601-1, 601-2 . . . 601-32 and to a one cycle delay cell 603 that generates a copy of the reference oscillating RF signal with one cycle delay as well as an inverted copy of the reference oscillating RF signal with the one cycle delay. The copy of the reference oscillating RF signal with the one cycle delay as generated by the one cycle delay cell 603 as well as the output of the last delay cell 601-32 is supplied to a phase detector circuit 605 whose output drives a series-coupled charge pump circuit 607, filter circuit 609 and bias generator circuit 611. The output of the bias generator circuit 611 is supplied to each one of the thirty-two delay cells 601-1, 601-2 . . . 601-32 and is configured such that the duty cycle of the oscillating RF signals produced by the delay cells 601-1, 601-2 . . . 601-32 matches the duty cycle of the reference oscillating RF signal. The inverted copy of the reference oscillating RF signal with the one cycle delay as generated by the one cycle delay cell 603 as well as the output of the intermediate delay cell 601-16 is supplied to a phase detector circuit 613 whose output drives a series-coupled charge pump circuit 615, filter circuit 617 and bias generator circuit 619. The output of the bias generator circuit 619 is supplied to each one of the thirty-two delay cells 601-1, 601-2 . . . 601-32 and is configured to minimize phase error such that the appropriate delay is produced by the thirty-two delay cells 601-1, 601-2 . . . 601-32. The outputs of the thirty-two delay cells 601-1, 601-2 . . . 601-32 are supplied to a 32-to-2 analog multiplexer 621 whose multiplexing operation is controlled by a 5-bit control signal supplied thereto. The two outputs of the analog multiplexer 621 carry the pulse signals ($\Phi$, $\Phi+\pi$) for output to the NMR transmitter 12 as described herein. The phase of the ($\Phi+\pi$) pulse signal is offset from the phase of the $\Phi$ pulse signal by 90 degrees.

Note that DLL of FIG. 6 is capable of generating a plurality of phases (32, in the illustrated embodiment) at the same time, and is capable of switching among them with no time delay. The DLL can be designed to lock at one cycle delay (and avoid other solutions when frequency changes) and respond quickly to the change of frequency.

Figure 7:
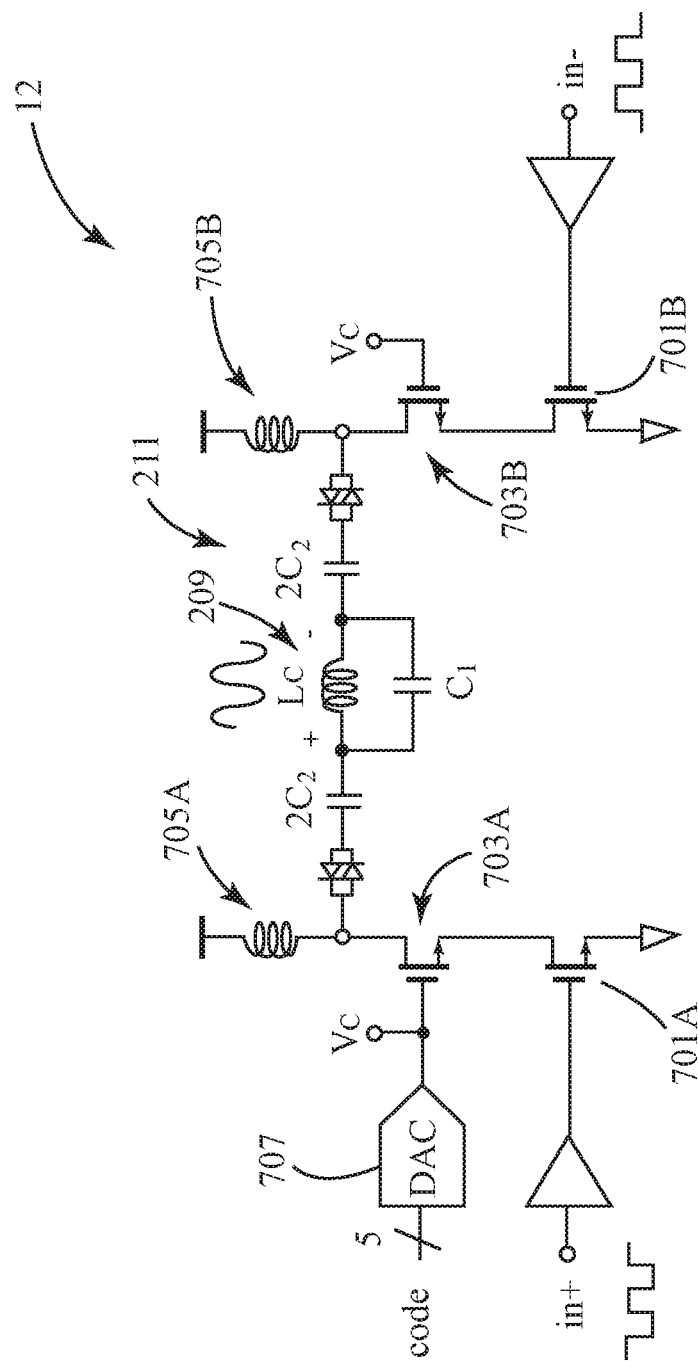
FIG. 7 is a schematic diagram of an embodiment of the NMR transmitter of the NMR ASIC of FIG. 2.

FIG. 7 shows an embodiment of the NMR transmitter 12 where the power amplifier function and the digitally-controlled variable attenuator function are folded into a single amplifier stage. The amplifier stage employs a Class E design with a differential input stage (transistors 701A and 701B) each employing a series-coupled cascode transistor (703A or 703B) and inductor (705A or 705B) as corresponding load elements. The Class E design is configured to cover a wide range of frequencies (unlike class D topology) as well as to reduce power consumption and heat generation, compared to linear PAs such as Class A or AB. The digitally-controlled variable attenuator function is realized by a digital-to-analog converter 707 whose output drives the gate of one of the cascode transistors (703A) and functions to provide variable attenuation of the differential RF pulse signal produced at the drains of the two cascode transistors (703A, 703B) for output to the external antenna 209. The level of attenuation can be selected between thirty-two levels as dictated by the 5-bit control signal or code supplied to the input of the digital-to-analog converter 707.

Figure 8:
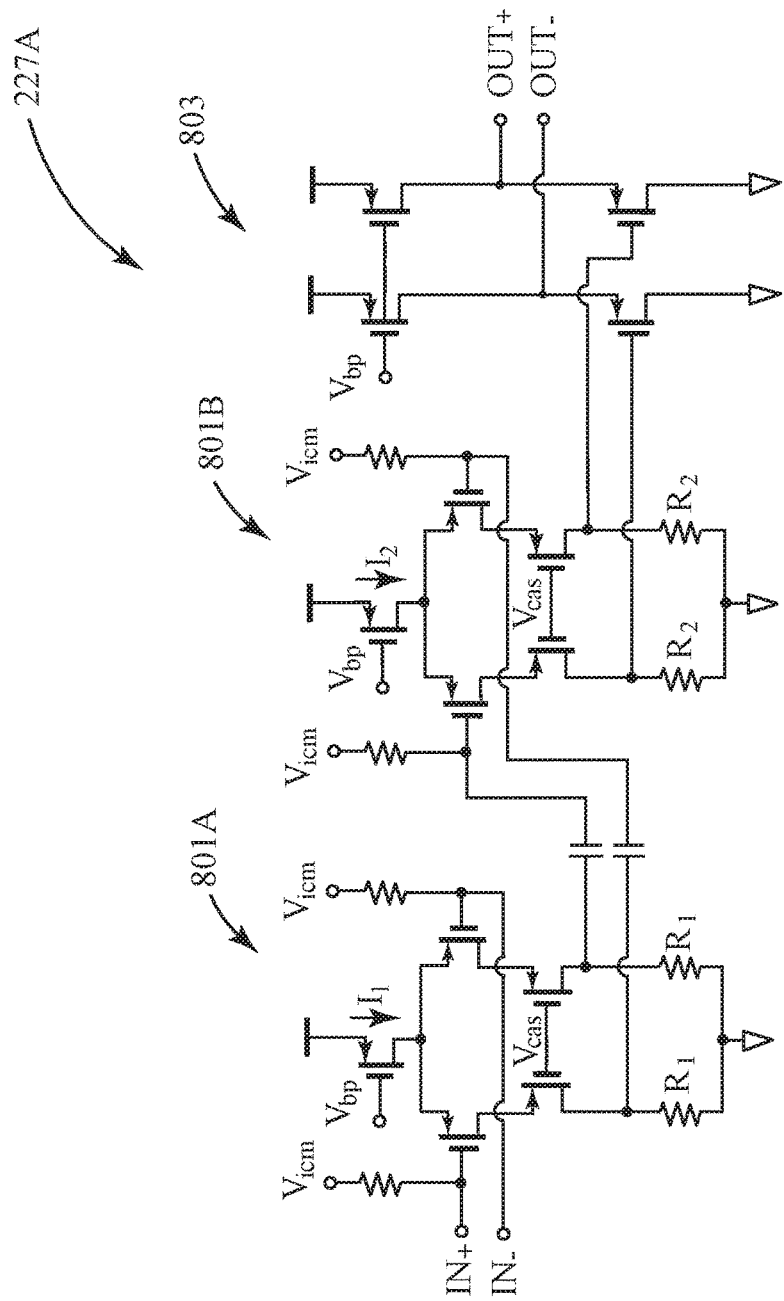
FIG. 8 is a schematic diagram of an embodiment of a power amplifier stage of the NMR receiver of the NMR ASIC of FIG. 2.

FIG. 8 shows an embodiment of the low-noise amplifier stage 227A of the NMR receiver 13 of FIG. 2, which includes two series-coupled differential amplifier stages 801A and 801B. The doubled-ended output of the differential amplifier stage 801B is coupled to a doubled-ended level shifting stage 803. The balanced structure of the series-coupled differential amplifier stages 801A and 801B provides for common mode noise rejection with a fixed differential signal gain of approximately 200 and with an input referred noise as low as 0.8 nV/sqrt(Hz). The biasing of the stages of the NMR receiver 13 can be temperature compensated so that the gain of the NMR receiver 13 is insensitive to expected variations in temperature during operation of the NMR ASIC 10. In one embodiment, the gain decreases by 4 dB as temperature increases from 25° C. to 150° C. This feature can improve performance of the NMR ASIC 10 at high temperatures.

Figure 9:
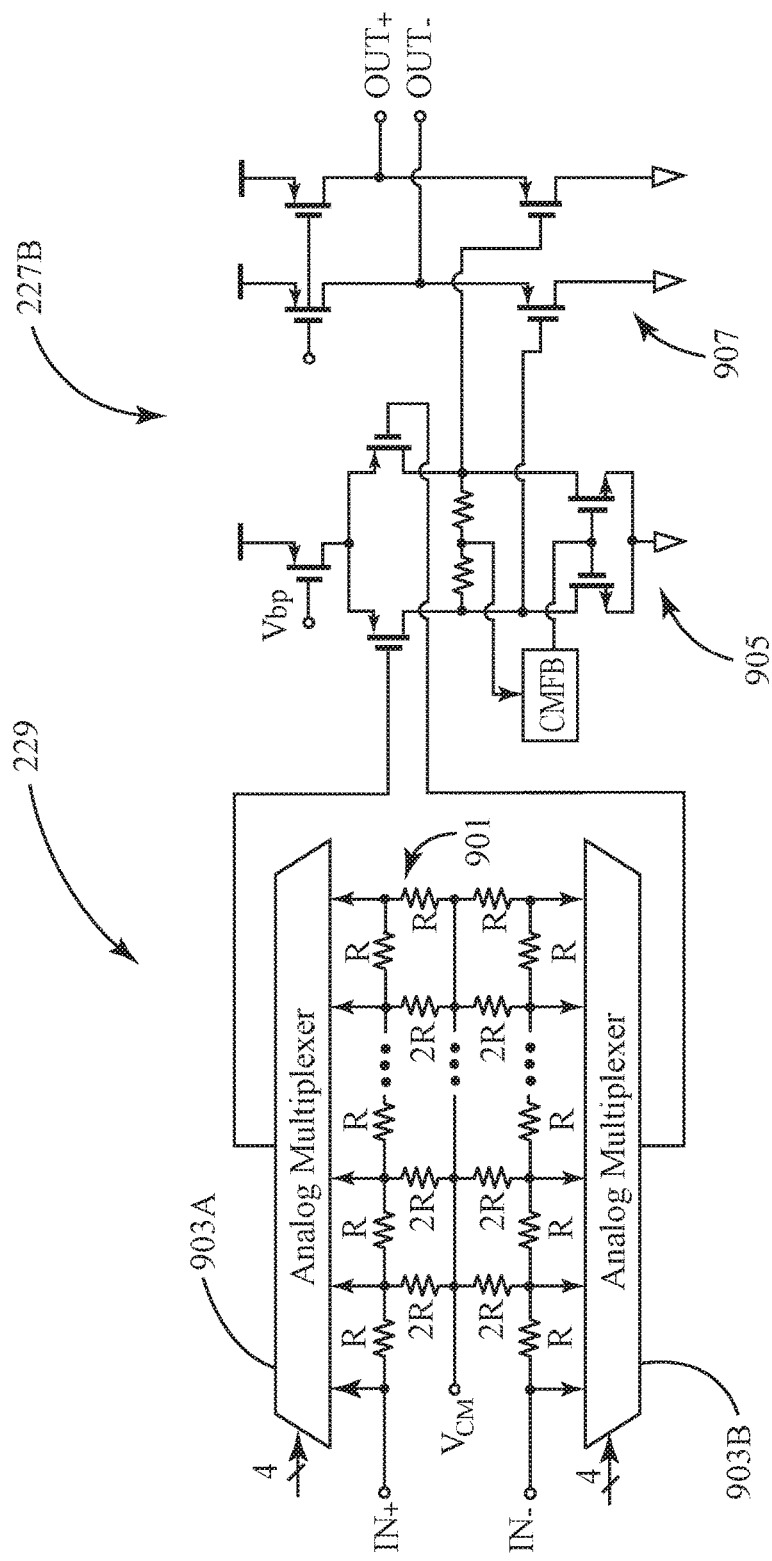
FIG. 9 is a schematic diagram of an embodiment of a digitally-controlled voltage attenuator and power amplifier stage of the NMR receiver of the NMR ASIC of FIG. 2.

FIG. 9 shown an embodiment of the digitally-controlled attenuator stage 229 and the low-noise amplifier stage 227B of the NMR receiver 13 of FIG. 2. The digitally-controlled attenuator stage 229 includes a resistor network 901 coupled between the differential inputs (IN+ and IN−) and the inputs of two analog multiplexers 903A, 903B. The multiplexing operations of the two analog multiplexers 903A, 903B is controlled by a 4-bit control signal supplied thereto and controls the attenuation level of the attenuator stage 229. In one embodiment, the level of attenuation can be controlled up to −72 dB at −6 dB step sizes, which allows a wide dynamic range which fits a variety of NMR experiments where spin concentration and volume vary. The differential signal output by the two analog multiplexers 903A, 903B is supplied to the inputs of the low-noise amplifier stage 227B. The low-noise amplifier stage 227B includes a single differential amplifier stage 905 coupled to a doubled-ended level shifting stage 907. The signal gain of the amplifier stages can be adaptively adjusted to the change of environmental temperature by a bias circuitry.

Figure 10:
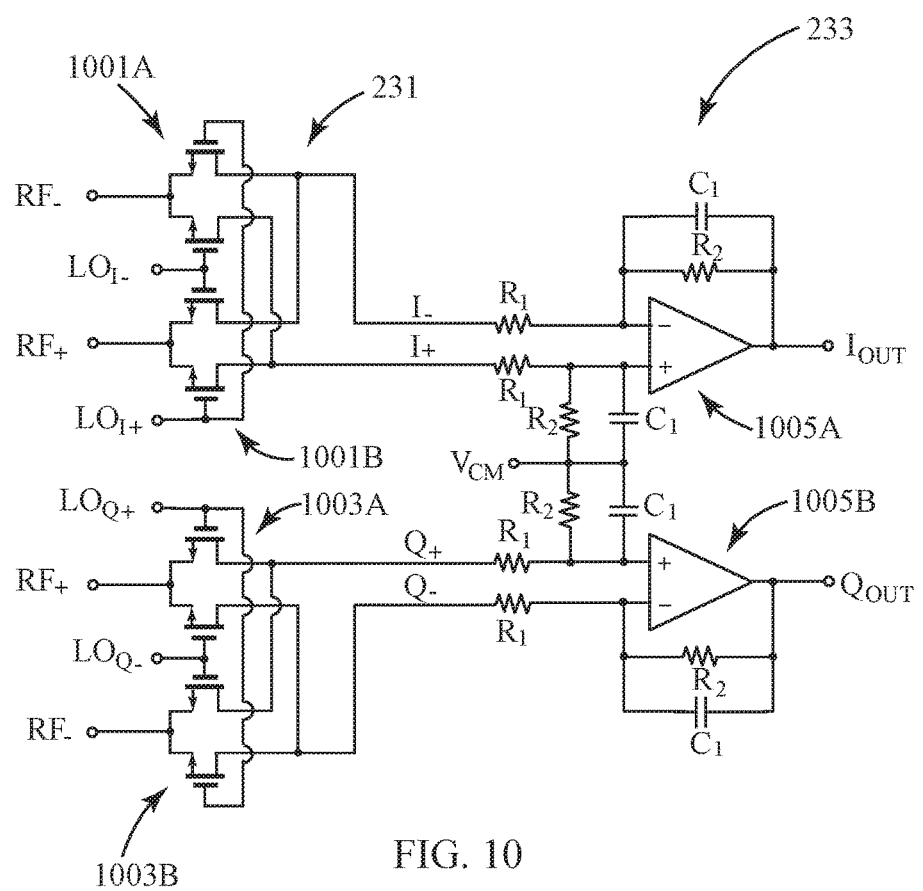
FIG. 10 is a schematic diagram of an embodiment of a quadrature heterodyne demodulator stage and low pass filter stage of the NMR receiver of the NMR ASIC of FIG. 2.

FIG. 10 shows an embodiment of the quadrature heterodyne demodulator stage 231 and the low pass filter stage 233 of the NMR receiver 13 of FIG. 2. The quadrature heterodyne demodulator stage 231 is supplied with the reference oscillating RF signal (labeled $LO_{I+}$ and $LO_{I-}$) as generated by the clock generator 217. The quadrature heterodyne demodulator stage 231 processes the amplified NMR signals output by the amplifier stage 227B (labeled $RF_+$ and $RF_-$) to generate in-phase signal components ($I_+$ and $I_-$) where the reference oscillating signal component ($LO_{I+}$ and $LO_{I-}$) is mixed with the amplified NMR signal output by the amplifier stage 227B ($RF_+$ and $RF_-$) as well as a quadrature-phase single components ($Q_+$ and $Q_-$) where the quadrature phase of the reference oscillating RF signal ($LO_{Q+}$ and $LO_{Q-}$) is mixed with the amplified NMR signal output by the amplifier stage 227B ($RF_+$ and $RF_-$). The mixing of the reference oscillating RF signal ($LO_{1+}$ and $LO_{I-}$) and the amplified NMR signal output by the amplifier stage 227B ($RF_+$ and $RF_-$) is accomplished by two pairs of transistors 1001A, 1001B that provide passive mixing at a constant gain of −3.9 dB or some other desired gain as dictated by the design of the transistors 1001A, 1001B. The mixing of the quadrature phase of the reference oscillating RF signal ($LO_{Q+}$ and $LO_{Q-}$) and the amplified NMR signal output by the amplifier stage 227B ($RF_+$ and $RF_-$) is also accomplished by two pairs of transistors 1003A, 1003B that provide passive mixing at a constant gain of −3.9 dB or some other desired gain as dictated by the design of the transistors 1003A, 1003B. Both the in-phase signal components ($I_+$ and $I_-$) and the quadrature phase signal components ($Q_+$ and $Q_-$) generated by the quadrature heterodyne demodulator stage 231 are subjected to low pass filtering by the low pass filter stage 233. The low pass filtering of the in-phase signal components ($I_+$ and $I_-$) can be accomplished by an op-amp filter circuit 1005A that provides for differential-to-singled-ended low pass filtering as shown. The cut-off frequency can be set at 500 kHz or some other desired frequency as dictated by the design of op-amp filter circuit 1005A. The low pass filtering of the quadrature-phase signal components ($Q_+$ and $Q_-$) can be accomplished by an op-amp filter circuit 1005B that provides for differential-to-singled-ended low pass filtering as shown. The cut-off frequency can be set at 500 kHz or some other desired frequency as dictated by the design of op-amp filter circuit 1005B. The filtered in-phase and quadrature phase signal components output by the low pass filter stage 233 ($I_{out}$ and $Q_{out}$) can be supplied to the signal processing circuitry 235 of FIG. 2 as described above.

Figure 11A:
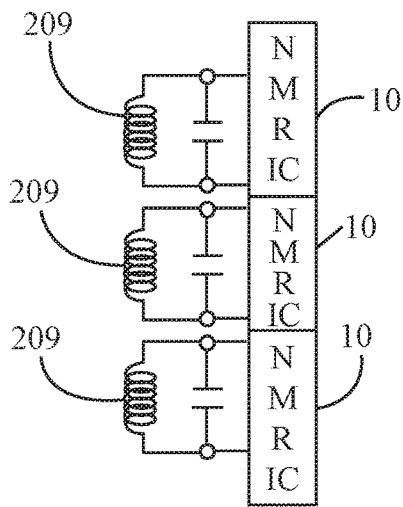
FIGS. 11A-C are schematic diagrams of different multi-channel NMR configurations that employ the NMR ASIC of FIG. 2.
Figure 11B:
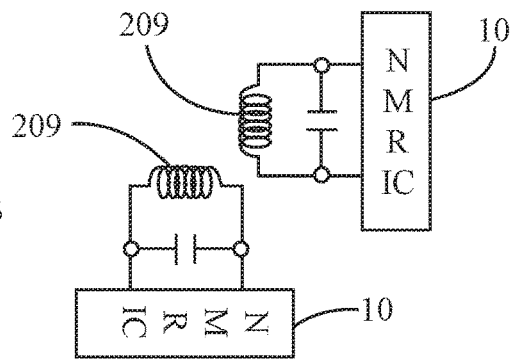
Figure 11C:
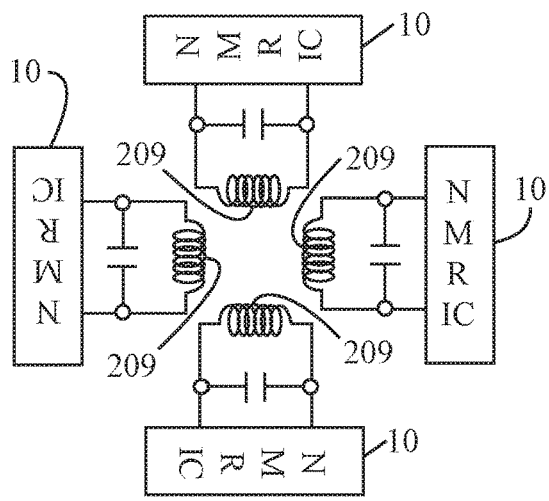

FIGS. 11A-C are schematic diagrams of different multi-channel NMR systems that employ the NMR ASIC of FIG. 2. FIG. 11A shows a system with three coils 209 arranged in a series configuration with three corresponding NMR ASICS 10. The NMR ASICS 10 can be configured to transmit NMR pulse sequences in parallel with one another for emission of parallel excitation signals from the series-coupled coils 209. These measurements can provide a high signal-to-noise ratio. Alternatively, the NMR ASICS 10 can be configured to transmit different NMR pulse sequences in parallel with one another for parallel emission of excitation signals for testing different spin species (such as $^1H$, $^{19}F$, etc.) with the series-coupled coils 209. FIG. 11B shows a system with two coils 209 arranged in a quadrature configuration (i.e., orientated ninety degrees relative to one another) with two corresponding NMR ASICS 10. The quadrature coils 209 can be positioned within the static magnetic field, $B_0$, for example, the axes of both coils are perpendicular to the direction of $B_0$. The NMR ASICS 10 can be configured to transmit NMR pulse sequences in parallel with one another for emission of parallel excitation signals from the quadrature coils 209. These measurements can provide a high signal-to-noise ratio. FIG. 11C shows a system with four coils 209 arranged in a phased array configuration with four corresponding NMR ASICS 10. The phased array coils 209 can be positioned within a static magnetic field, $B_0$, for example, the axes of both coils are perpendicular to the direction of $B_0$. The NMR ASICS 10 can be configured to transmit NMR pulse sequences in parallel with one another for emission of parallel excitation signals from the phased array coils 209. These measurements can provide a high signal-to-noise ratio.

Figure 12:
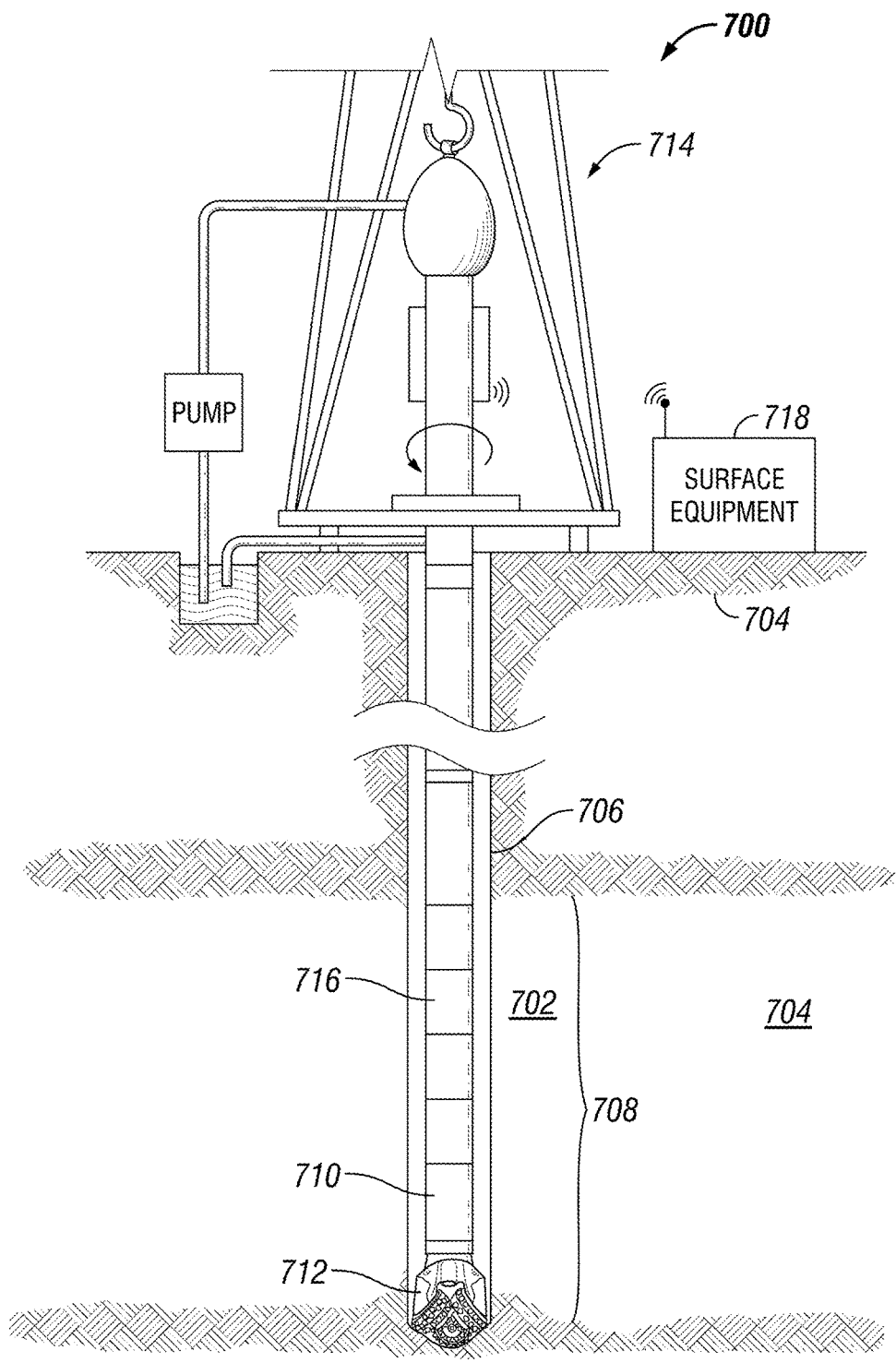
FIG. 12 shows a logging-while-drilling (LWD) system in accordance with one embodiment of the present disclosure.

Illustrative embodiments of the present disclosure are further directed to oil and gas field applications, such as wellbore logging tools. In particular, FIG. 12 shows a logging-while-drilling (LWD) system 700 for investigating, in situ, a substance 702 within an earth formation 704 and determining a property of the substance, while a drilling operation is performed. The LWD system 700 includes a drill string 708. The drill string 708 is disposed within a wellbore 706 that traverses the formation 704. The drill string 708 includes a drill collar 710 with a drill bit 712 disposed at the lower-end of the drill collar. The LWD system 700 also includes a surface system with a derrick assembly and platform assembly 714 positioned over the wellbore 706. The derrick assembly 714 rotates the drill string 708 and, as the drill string rotates, the drill bit 712 drills deeper into the wellbore 706. An LWD NMR logging module 716 is disposed within the drill collar 710 so that the module can log the surrounding earth formation as the drilling operation is performed. The logging module 716 communicates with surface equipment 718, which includes an operator interface for communicating with the module. In various embodiments, the NMR logging module 716 and operator interface can communicate via any one of a wired-drill pipe connection, an acoustic telemetry connection, optical communication and/or electronic communication.

Figure 13:
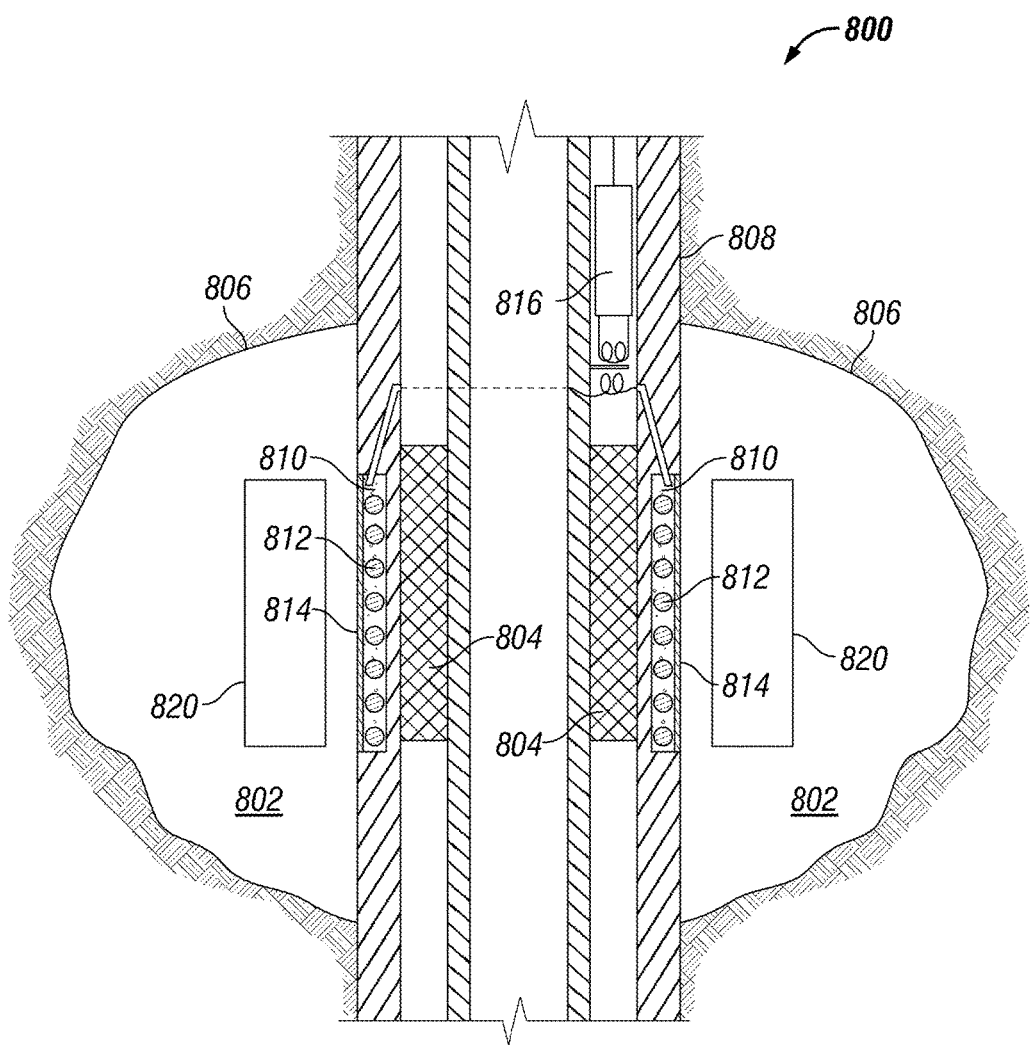
FIG. 13 shows a LWD NMR logging module in accordance with one embodiment of the present disclosure.

FIG. 13 shows an LWD NMR logging module 800 for applying NMR pulse sequences to the formation. The module 800 includes magnet sections 804 that generate a static magnetic field within a zone of sensitivity 806 within the formation 802. The module 800 also includes a drill collar 808 with an axial slot 810. A coil 812 is disposed within the axial slot 810 and the slot is filled with an insulator, such as ceramic, epoxy, or fiberglass. As explained above, the coil 812 includes two coil sections arranged in opposite polarity. The coil sections are wound around the drill collar 808 within the axial slot 810. The axial slot 810 is sealed using a cover 814. In some embodiments, the cover 814 is formed from a non-magnetic material and/or non-conductive material. At one end, the coil sections are grounded (e.g., to the drill collar 808). At the other end, the coil sections are coupled to NMR electronics 816, which includes an IC-based NMR spectrometer 100, as described in, for example, FIGS. 1 and 2. The NMR electronics 816 are coupled to the coil 812 via, for example, pressure feed-throughs. The coil 812 applies an oscillating magnetic field (e.g., NMR pulse sequences) to an area of interest 820 within the zone of sensitivity 806 of the formation 802. In some embodiments, the oscillating magnetic field is axially symmetric to facilitate measurements during rotation of the drill string. Further details of NMR LWD systems are described in U.S. Pat. No. 5,629,623 issued on May 13, 1997 and U.S. Pat. No. 6,392,410, issued on May 21, 2002. Each of these patents is incorporated by reference herein in their entireties. One specific example of a NMR LWD tool is Schlumberger's proVISION™ tool.

The IC-based NMR systems described above provide a number of advantages over commercially available NMR systems. An NMR integrated circuit as described herein integrates main components within a tiny area so that it does not need long and unnecessary interconnects. Interconnects can generate many problems including parasitic components, electromagnetic interferences, noise due to the resistance of the wire and timing disparity of signals. Due to its small size, an NMR integrated circuit can be placed very close to the external coil. In terms of signal-to-noise ratio, this is very helpful since noises generated from cable and impedance transformation network can be reduced.

An NMR integrated circuit as described herein also has a tremendous advantage in size over other commercial spectrometers. Also, the efficiently designed switching power amplifier and low power features (power off when not enabled), described above, lead to low power consumption. With these two features combined, the entire NMR system can be made very small and portable, and can be placed wherever needed for chemical, biological or other experiments.

Since the NMR integrated circuit as described herein is configurable through a simple data communication interface, multi-channel NMR systems can be easily formed. In particular, a highly parallelized system can be implemented in which each NMR integrated circuit has control over its own channel.

In one embodiment, multiple channels may operate in the following manner. Pulse sequences for each channel can be downloaded through the data communication interface of the respective NMR integrated circuits. When a single Enable signal, which is connected to all the NMR integrated circuits, is activated, each one of the NMR channels can start running its own pulse sequence synchronously. In this way, tight synchronization among multiple channels is possible. This is especially useful for multi-channel heteronuclear experiments (INEPT, NOESY, HMQC).

Advantageously, the pulse sequence generator of the NMR integrated circuit is capable of performing arbitrary pulse sequences. This is an advantage in NMR applications that seek to perform different and complex sequences, including NMR spectroscopy, diffusion, multi-dimensional experiments, and multi-channel (multi-nuclei, such as carbon-proton) NMR.

Furthermore, the NMR integrated circuit has many applications in the oilfield, including the analysis of rocks cores either downhole in a special core measurement module, or in a laboratory or a well-site system. In a laboratory environment, the conventional NMR system uses discrete electronic components and, as a result, the electronics are bulky and expensive. The NMR ASIC can replace much of the bulky electronics and perform NMR measurement of rock cores. In the downhole environment, the NMR ASIC can be integrated as part of a logging tool. For example, it can be integrated as part of an NMR core analyzer module of a downhole coring tool. The downhole coring tool extracts a rock core sample from the wellbore and transports the sample into the NMR core analyzer module. Once it is in the module, the NMR ASIC can be used to perform a series of NMR measurements on the rock core. The use of the NMR ASIC can significantly reduce the volume of the electronics and thus reduce cost. A further application is in the laboratory or downhole measurement of crude oil samples. In particular, it is important to perform such measurements in downhole conditions since the crude oil may change its properties if the sample is broughtuphole, resulting in changes of pressure and temperature.

The NMR ASIC has other application beyond oilfield applications. In various embodiments, the programmability of the pulse sequencer of the NMR ASIC allows the NMR ASIC to employ a wide range of pulse sequences as part of the NMR experiments performed by the NMR ASIC. This is a major distinction with regard to prior art systems where the pulse sequences are limited to CPMG. This feature thus allows for the NMR ASIC to perform multi-dimensional spectroscopy experiments as well as multi-dimensional relaxation and diffusion experiments.

The NMR ASIC has other applications in material/fluid characterization using small-size or mobile NMR devices where the reduced size of the electronics is particularly useful. For example, the NMR ASIC can be part of a small-size or micro-NMR system using small or micro NMR coils (such as 0.1 mm diameter capillary and microfluidic devices, such as lab-on-a-chip). Such small-size or micro-NMR systems can be used in conjunction with a conventional high field magnet in order to perform high throughput NMR spectroscopy, or they can be used with small magnets (often based on permanent magnets) to become low cost and portable NMR systems.

Since the output RF power of the NMR ASIC is limited by design, for larger sample sizes, it may be beneficial to direct the output of the NMR transmitter of the NMR ASIC to an external RF amplifier. In this configuration, the external RF amplifier is coupled between the NMR transmitter of the NMR ASIC and the external antenna. The external RF amplifier can boost the RF power of the excitation signals to cover the larger sample size as needed.

The components, steps, features, objects, benefits and advantages that have been disclosed are merely illustrative. None of them, nor the discussions relating to them, are intended to limit the scope of protection in any way. Numerous other embodiments are also contemplated, including embodiments that have fewer, additional, and/or different components, steps, features, objects, benefits and advantages.

Nothing that has been stated or illustrated is intended to cause a dedication of any component, step, feature, object, benefit, advantage, or equivalent to the public. While the specification describes particular embodiments of the present disclosure, those of ordinary skill can devise variations of the present disclosure without departing from the inventive concepts disclosed in the disclosure.

In the present application, reference to an element in the singular is not intended to mean "one and only one" unless specifically so stated, but rather "one or more." All structural and functional equivalents to the elements of the various embodiments described throughout this disclosure, known or later come to be known to those of ordinary skill in the art, are expressly incorporated herein by reference.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims.

What is claimed is:

1. An integrated circuit for use with an external antenna and an external host system, the integrated circuit comprising:
 a memory circuit;
 a data communication interface to the external host system, wherein the data communication interface is configured to receive parameter data for at least one NMR pulse sequence from the host system and transfer the received parameter data to the memory circuit such that the memory circuit stores the parameter data for the at least one NMR pulse sequence, wherein the parameter data pertains to an excitation period, a delay period without excitation, and an acquisition period that are part of a corresponding NMR pulse sequence;
 a pulse sequencer and NMR transmitter circuit that cooperate to generate radio frequency (RF) signals in accordance with the parameter data stored in the memory circuit, wherein the integrated circuit is configured to supply the RF signals to the external antenna for emitting excitation signals from the external antenna during the excitation period of the corresponding NMR pulse sequence; and
 an NMR receiver circuit for receiving electrical signals generated by the external antenna during the acquisition period of the corresponding NMR pulse sequence;
 wherein the memory circuit, data communication interface, pulse sequencer, NMR transmitter circuit, and NMR receiver circuit are all integrated as parts of a single integrated circuit chip; and
 wherein the parameter data comprises data that specifies a pulse amplitude for the excitation signals emitted from the external antenna during the excitation period of the corresponding NMR pulse sequence.

2. An integrated circuit according to claim 1, wherein:
 the parameter data further comprises additional data that specifies at least one of (i) a time duration for the excitation period of the corresponding NMR pulse sequence, (ii) a pulse phase for said excitation signals of the corresponding NMR pulse sequence, (iii) a time duration for the acquisition period of the corresponding NMR pulse sequence, (iv) a time duration for the delay period without acquisition of the corresponding NMR pulse sequence, (v) a time period between the excitation period and the acquisition period of the corresponding NMR pulse sequence, (vi) a loop start and a loop end for a loop of NMR pulse sequences, and (vii) information that enables or disables the NMR receiver during the acquisition period of the corresponding NMR pulse sequence.

3. An integrated circuit according to claim 1, wherein the data communication interface employs a standard communication protocol.

4. An integrated circuit according to claim 1, wherein:
 the data communication interface comprises a serial peripheral interface that supports synchronous serial data communication from the host system.

5. An integrated circuit according to claim 1, further comprising:
 at least one output port for outputting electrical signals in analog form as generated by the NMR receiver circuit.

6. An integrated circuit according to claim 1, further comprising:
 an input port that is configured to input a reference oscillating RF signal.

7. An integrated circuit according to claim 6, wherein:
 the NMR transmitter circuit is configured to generate a pulse of an oscillating RF signal at a digitally-controlled phase offset relative to the reference oscillating RF signal, wherein the digital-controlled phase offset is dictated by parameter data stored by the memory circuit.

8. An integrated circuit according to claim 7, wherein:
 the NMR transmitter circuit is further configured to generate an oscillating RF signal at a phase offset by ninety degrees relative to said digitally-controlled phase offset.

9. An integrated circuit according to claim 7, further comprising:
 a multiphase generator realized by a delayed lock loop having a plurality of series-coupled delay cells whose outputs are coupled to a digitally-controlled multiplexer, wherein said digitally-controlled multiplexer is configured to operate under control of parameter data stored by the memory circuit that represents said digitally-controlled phase offset.

10. An integrated circuit according to claim 1, wherein:
 said NMR transmitter circuit includes a digitally-controlled voltage attenuator that provides for controlled voltage attenuation of at least one oscillating RF signal output from said NMR transmitter circuit, wherein said digitally-controlled voltage attenuator is configured to operate under control of parameter data stored by the memory circuit.

11. An integrated circuit according to claim 10, wherein:
 said digitally-controlled voltage attenuator comprises a cascode transistor that is part of a power amplifier stage, where said cascode transistor has a gate electrode that is operably coupled to a digital-to-analog converter, wherein said digital-to-analog converter and said cascode transistor cooperate to provide controlled voltage attenuation of at least one oscillating RF signal output from said power amplifier stage according to a digital control signal supplied to said digital-to-analog converter, wherein said digital control signal is based on user defined parameter data stored by the memory circuit.

12. An integrated circuit according to claim 10, wherein:
 said digitally-controlled voltage attenuator is controlled according to data values of the data elements stored as part of parameter data, where such data values represent pulse amplitude for said excitation signals of the NMR pulse sequence.

13. An integrated circuit according to claim 1, wherein:
 said NMR receiver circuit includes a digitally-controlled voltage attenuator that provides for controlled voltage attenuation of at least one electrical signal derived from the external antenna during the acquisition period of the NMR pulse sequence, wherein said digitally-controlled voltage attenuator is configured to operate under control of parameter data stored by the memory circuit.

14. An integrated circuit according to claim 13, wherein:
 said NMR receiver circuit further includes two fixed-gain amplifier stages, and said digitally-controlled voltage attenuator is operably disposed between said two fixed-gain amplifier stages.

15. An integrated circuit according to claim 13, wherein:
said digitally-controlled attenuator includes a resistor network operably coupled to at least one analog multiplexer that is controlled by digital control signals supplied thereto.

16. An integrated circuit according to claim 1, wherein:
said pulse sequencer is configured to initiate NMR experiments involving the corresponding NMR pulse sequence in response to an Enable signal communicated to said integrated circuit.

17. An integrated circuit according to claim 1, wherein the integrated circuit is part of a wellbore tool.

18. An integrated circuit according to claim 1, wherein the integrated circuit is configured to perform at least one of a multi-dimensional spectroscopy experiment and a multi-dimensional relaxation and diffusion experiment.

19. An integrated circuit according to claim 1, wherein the integrated circuit is part of a laboratory NMR apparatus or a small-size NMR apparatus or a portable NMR apparatus.

20. An integrated circuit according to claim 1, wherein:
the parameter data stored by the memory circuit comprises data that corresponds to a plurality of NMR pulse sequences and that allows for varying pulse amplitude over the plurality of NMR pulse sequences.

21. An integrated circuit according to claim 20, wherein:
the parameter data stored by the memory circuit further includes additional data that corresponds to the plurality of NMR pulse sequences and that allows for at least one of: i) varying time duration of the excitation period over a plurality of NMR pulse sequences, ii) varying pulse phase for excitation signals over a plurality of NMR pulse sequences, (iii) varying time duration of the acquisition period over a plurality of NMR pulse sequences, (iv) varying time duration of the delay period without acquisition over a plurality of NMR pulse sequences, and (v) varying time period between the excitation period and the acquisition period over a plurality of NMR pulse sequences.

22. An integrated circuit according to claim 1, wherein:
said pulse sequencer includes a multiphase generator that generates a sequence of pulses of an oscillating RF signal under control of the parameter data stored by the memory circuit; and
said NMR transmitter circuit includes circuitry that adjusts amplitude of the sequence of pulses of the oscillating RF signal output from the multiphase generator under control of the parameter data stored by the memory circuit.

23. A multi-channel NMR system comprising:
a host system; and
a plurality of integrated circuits, each respective integrated circuit including
  i) a memory circuit,
  ii) a data communication interface to the host system, wherein the data communication interface is configured to receive parameter data for at least one NMR pulse sequence from the host system and transfer the received parameter data to the memory circuit such that the memory circuit stores the parameter data for the at least one NMR pulse sequence, wherein the parameter data pertains to an excitation period, a delay period without acquisition, and an acquisition period that are part of a corresponding NMR pulse sequence,
  iii) a pulse sequencer and NMR transmitter circuit that cooperate to generate radio frequency (RF) signals in accordance with the parameter data stored in the memory circuit, wherein the integrated circuit is configured to supply the RF signals to an external antenna for emitting excitation signals from the external antenna during the excitation period of the corresponding NMR pulse sequence, and
  iv) an NMR receiver circuit for receiving electrical signals generated by the external antenna during the acquisition period of the corresponding NMR pulse sequence;
wherein the memory circuit, data communication interface, pulse sequencer, NMR transmitter circuit, and NMR receiver circuit of each respective integrated circuit are all integrated as parts of a single integrated circuit chip; and
wherein the pulse sequencer of each respective integrated circuit is configured to initiate NMR experiments involving the corresponding NMR pulse sequence according to the parameter data stored in the memory circuit of the respective integrated circuit in response to an Enable signal communicated to the respective integrated circuit.

24. An NMR apparatus comprising:
a host system;
at least one integrated circuit, the integrated circuit including
  i) a memory circuit,
  ii) a data communication interface to the host system, wherein the data communication interface is configured to receive parameter data for at least one NMR pulse sequence from the host system and transfer the received parameter data to the memory circuit such that the memory circuit stores the parameter data for the at least one NMR sequence, wherein the parameter data pertains to an excitation period, a delay period without excitation, and an acquisition period that are part of a corresponding NMR pulse sequence,
  iii) a pulse sequencer and NMR transmitter circuit that cooperate to generate radio frequency (RF) signals in accordance with the parameter data stored in the memory circuit, wherein the integrated circuit is configured to supply the RF signals to an external antenna for emitting excitation signals from the external antenna during the excitation period of the corresponding NMR pulse sequence, and
  iv) an NMR receiver circuit for receiving electrical signals generated by the external antenna during the acquisition period of the corresponding NMR pulsed;
wherein the memory circuit, data communication interface, pulse sequencer, NMR transmitter circuit, and NMR receiver circuit are all integrated as parts of a single integrated circuit chip; and
wherein the parameter data comprises data that specifies a pulse amplitude for the excitation signals emitted from the external antenna during the excitation period of the corresponding NMR pulse sequence.

25. An NMR apparatus according to claim 24, wherein:
said at least one integrated circuit further includes at least one output port for outputting electrical signals in analog form as generated by the NMR receiver circuit of the integrated circuit; and
the NMR apparatus further includes signal processing circuitry, operably coupled to said at least one output port, for processing the electrical signals output from said output port.

26. An NMR apparatus according to claim 24, wherein the NMR apparatus is part of a wellbore tool.

27. An NMR apparatus according to claim 24, further comprising:
an external RF amplifier operably coupled between the NMR transmitter of the integrated circuit and the external antenna.

28. An integrated circuit for use with an external antenna and an external host system, the integrated circuit comprising:
a memory circuit;
a data communication interface to the external host system, wherein the data communication interface is configured to receive parameter data for at least one NMR pulse sequence from the host system and transfer the received parameter data to the memory circuit such that the memory circuit stores the parameter data for the at least one NMR pulse sequence, wherein the parameter data pertains to an excitation period, a delay period without excitation, and an acquisition period that are part of a corresponding NMR pulse sequence;
a pulse sequencer and NMR transmitter circuit that cooperate to generate radio frequency (RF) signals in accordance with the parameter data stored in the memory circuit, wherein the integrated circuit is configured to supply the RF signals to the external antenna for emitting excitation signals from the external antenna during the excitation period of the corresponding NMR pulse sequence; and
an NMR receiver circuit for receiving electrical signals generated by the external antenna during the acquisition period of the corresponding NMR pulse sequence;
wherein the memory circuit, data communication interface, pulse sequencer, NMR transmitter circuit, and NMR receiver circuit are all integrated as parts of a single integrated circuit chip; and
wherein the parameter data stored by the memory circuit includes data that corresponds to a plurality of NMR pulse sequences and that allows for varying pulse amplitude over the plurality of NMR pulse sequences.

29. An integrated circuit according to claim 28, wherein:
the parameter data stored by the memory circuit further includes additional data that corresponds to the plurality of NMR pulse sequences and that allows for at least one of: i) varying time duration of the excitation period over a plurality of NMR pulse sequences, ii) varying pulse phase for excitation signals over a plurality of NMR pulse sequences, (iii) varying time duration of the acquisition period over a plurality of NMR pulse sequences, (iv) varying time duration of the delay period without acquisition over a plurality of NMR pulse sequences, and (v) varying time period between the excitation period and the acquisition period over a plurality of NMR pulse sequences.

* * * * *